United States Patent [19]

Ito et al.

[11] Patent Number: 5,399,145
[45] Date of Patent: Mar. 21, 1995

[54] BLOOD PUMP

[75] Inventors: Kazuyuki Ito; Michiharu Nakao; Takeshi Aizawa, all of Shizuoka, Japan; Yukihiko Nose, Houston, Tex.

[73] Assignee: Nikkiso Company Limited, Tokyo, Japan

[21] Appl. No.: 108,251

[22] Filed: Aug. 19, 1993

[30] Foreign Application Priority Data

Aug. 20, 1992 [JP] Japan ................................. 4-221741

[51] Int. Cl.$^6$ ............................................. F04D 7/02
[52] U.S. Cl. ..................................................... 600/16
[58] Field of Search ............... 417/423.1, 423.8, 423.9, 417/424.1, 424.2; 600/16, 17

[56] References Cited

U.S. PATENT DOCUMENTS

| 3,090,320 | 5/1963 | Hummer et al. | |
| 4,135,253 | 1/1979 | Reich et al. | |
| 4,927,407 | 5/1990 | Dorman | 600/16 |
| 4,984,972 | 1/1991 | Clauseu et al. | |
| 5,145,333 | 9/1992 | Smith | 600/16 |

FOREIGN PATENT DOCUMENTS

| 480524 | 2/1938 | United Kingdom . |
| 9015640 | 12/1990 | WIPO . |

*Primary Examiner*—William E. Kamm
*Assistant Examiner*—Marianne Parker
*Attorney, Agent, or Firm*—Browdy and Neimark

[57] ABSTRACT

A novel cardiac assist blood pump is disclosed. The blood pump comprises a pump chamber, a pressurizing chamber provided adjacent to the pump chamber, a rotor chamber provided adjacent to the pressurizing chamber and an impelled positioned in the pump chamber, said pump being characterized in that the rotation shaft of the impeller means is provided with a first seal member having a skirt portion which is made of an elastomeric material and extends downward to cover the clearance between the rotation shaft and the first rotation shaft hole provided between the pump chamber and the pressurizing chamber and a second seal member similar to the first one which covers the clearance between the rotation shaft and the second rotation shaft hole provided between the pressurizing chamber and the rotor chamber; and tile pressurizing liquid is forced into the pressurizing chamber. The pressurizing liquid penetrates into the pump chamber through the clearance between the rotation shaft and the rotation shaft hole and lifts the skirt portion of the first seal member and the friction between the seal member and tile bottom of the pump chamber is prevented. Also the pressurizing liquid presses the skirt portion of the second seal member and thus prevents leakage of tile pressurizing liquid into the rotor chamber.

8 Claims, 1 Drawing Sheet

BLOOD PUMP

BACKGROUND OF THE INVENTION

1. Field of the Invention

The present invention relates to a blood pump, which used as a cardiac assist device. More particularly, this invention relates to a blood pump, which is free from leakage of blood from the pump chamber and occurrence of hemolysis and clotting in use.

2. Prior Art

There have been known blood pumps, which comprise a pump chamber provided with a blood inlet port at the top thereof and a blood outlet port provided in the direction perpendicular to the axis of the blood inlet port and an impeller which comprises a base plate (hub) and blades provided on the base plate generally uprightly and generally radially and is secured to a rotation shaft and rotatably installed in the pump chamber.

In blood pumps of this type, the blood introduced through the inlet port is discharged through the outlet port by the rotation of the impeller.

In blood pumps of this type, the sealing between the rotation shaft of the impeller and the rotation shaft hole provided in the bottom of the pump chamber is effected with a mechanical means. As a result, the high speed rotation of the impeller generates heat because of the friction between the seal member and the rotation shaft or the surface of the pump chamber bottom depending on the structure. The frictional heat may promote hemolysis or cause clotting. Therefore, blood pumps of this type have defect that they cannot bear prolonged operation.

A clotting-prevention type blood pump, which is intended to solve the above problem, is disclosed in Japanese Laid-Open Patent Publication No. Sho 61-500058, which corresponds to PCT application.

In this clotting-prevention type blood pump, the bearing, which rotatably supports the impeller shaft positioned in the impeller chamber, is constructed hydrodynamically. That is, through the clearance between the rotation shaft and the surrounding supporting section, a pressurized sealing fluid penetrates into the impeller chamber. By the penetration of the fluid into the impeller chamber, prevention of leakage of blood out of the impeller chamber is intended.

In this cloting-prevention type blood pump, however, if the pressure in the impeller chamber and the pressure of the sealing fluid are inverted, or if the sealing fluid is not sufficiently supplied, blood will leak through said clearance. This means that the sealing is not only impaired but the leaking blood may clot in the impeller mechanism, which will hinder smooth rotation of the impeller and thus make difficult the continuous normal operation of the blood pump. Thus problems troublesome for the blood pump such as hemolysis and thrombosis are caused.

The present invention was made to solve the above-described problems. That is, it is the object of the present invention to provide a blood pump which can normally operate even when the pressure in the pump chamber (impeller chamber) and the pressure of sealing liquid are inverted and is free from occurrence of hemolysis and thrombosis.

DISCLOSURE OF THE INVENTION

In order to solve the above-described problems, the present invention provides a blood pump comprising a pump chamber having a blood inlet and a blood outlet; a pressurizing chamber provided adjacent to the pump chamber; a rotor chamber provided adjacent to the pressurizing chamber and an impeller means, which is comprised of a rotation shaft rotatably supported at center of the bottom of the rotor chamber, extends into the pump chamber through rotor shaft holes provided at the centers of the bottom of the pressurizing chamber and the bottom of the pump chamber and an impeller secured to the top of the rotation shaft, said impeller comprising a base plate with a plurality of impeller blades provided generally radially on the base plate; wherein the rotation shaft is provided with a first annular seal member which is mounted at the upper side of the bottom of the pump chamber and has an umbrella-shaped skirt portion made of an elastomeric material and extending from the lower part thereof toward the surface of the bottom of the pump chamber so as to cover the clearance of the rotation shaft and the rotation shaft hole and a second similar seal member which is mounted at the upper side of the bottom of the pressurizing chamber and has an umbrella-shaped skirt portion extending from the lower part thereof toward the surface of the bottom of the pressurizing chamber so as to cover the clearance of the rotation shaft and the rotation shaft hole.

The blood pump per se is made of a suitable material such as metal, plastic, etc. known among those skilled in the art.

Usually the blood pump is generally of a conical shape and the blood inlet port is provided at the top of the pump chamber and the blood outlet port is provided at the side thereof and the pressurizing chamber and the rotor chamber are of the cylindrical shape. But the shape is not limited thereto.

At least the skirt portion of the annular seal members are made of an elastomeric material which has no adverse effect against blood. Preferably and usually the seal member is made of an elastomeric material integrally with the skirt portion. Such materials are well known among those skilled in the art. One of the most preferable materials is silicone rubber or flooro rubber.

The base plate of the impeller is generally circular and may be conical. The impeller blades provided on the base plate generally uprightly and generally radially. This means the blade may be slightly inclined and may be deviated from the diametric direction.

The base plate of the impeller may be provided with through holes between the blades which enable the blood to flow from the underside of the plate to the upper side.

The pressurizing (sealing) liquid is a physiological solution, preferably a physiological saline solution containing an anti-clotting agent. One of the preferable anti-clotting agent is heparine.

In accordance with the present invention, the pressurizing chamber is filled with the pressurizing liquid which has a pressure higher than the liquid in the pump chamber and, therefore, the sealing liquid, which penetrates into the pump chamber, lifts the edge of the skirt portion of the seal member so that the edge of the portion does not contact the surface of the bottom of the pump chamber. Thus heat generation caused by the friction between the skirt portion and the bottom surface of the pump chamber and hemolysis resulting therefrom are prevented.

By using a pressurizing liquid containing an anti-clotting agent, clotting at the vicinity of the skirt portion of the first seal member is prevented by the pressurizing liquid, which has penetrated into the pump chamber.

Although the pressurizing liquid is forced into the pressurizing chamber, if the pressure in the pump chamber becomes higher than the pressure of the pressurizing chamber for some reason, the edge of the first seal member is pressed onto the surface of the bottom of the pump chamber by virtue of the resilient force thereof and, therefore, leakage of blood through the clearance between the first rotation shaft hole and the rotation shaft is prevented.

In the pressurizing chamber, the skirt portion of the second seal member is pressed onto the surface of the bottom of the pressurizing chamber by the pressure of the pressurizing liquid and, therefore, leakage of the pressurizing liquid through the clearance between the second rotation shaft hole and the rotation shaft is prevented.

BRIEF DESCRIPTION OF THE DRAWING

The attached

DESCRIPTION OF SPECIFIC EMBODIMENT OF THE INVENTION

Figure 1:
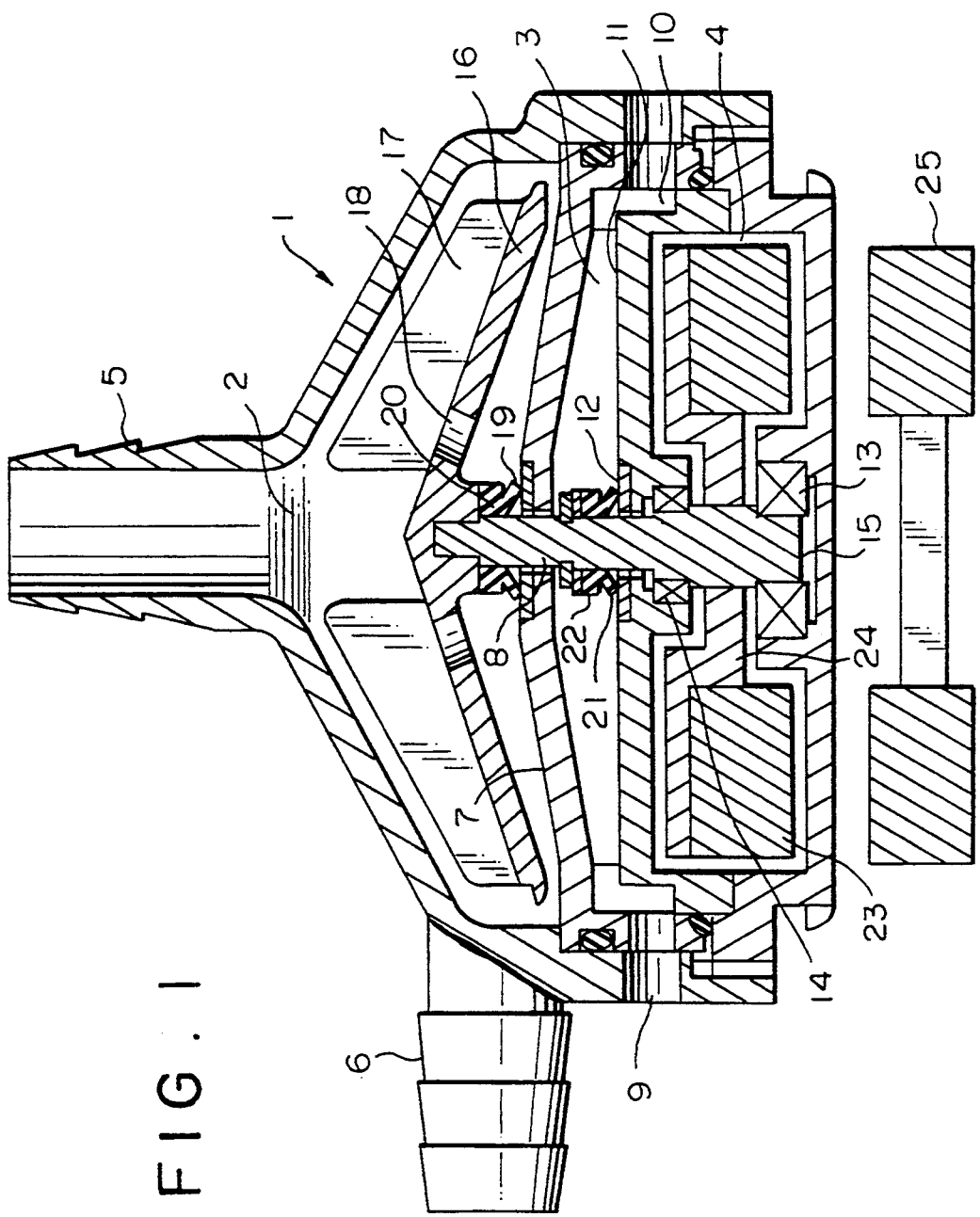
FIG. 1 is a cross-sectional view of an embodiment of the present invention.

Now the invention will be specifically described with reference to the attached drawing. Needless to say, however, the invention is not limited to this embodiment but can be suitably modified within the gist of the claimed technical idea.

FIG. 1 is a cross-sectional view of an example of the blood pump of this invention.

As shown there, the pump 1 comprises a pump chamber 2, pressurizing chamber 3 and a rotor chamber 4 which houses a rotor with magnets, which are driving means.

The pump chamber is generally of the shape of an inverted funnel. A blood inlet port 5 is provided at the top thereof and a blood outlet port 6 is provided at the side thereof. The bottom 7 of the pump chamber is generally circular and a first rotation shaft hole 8 is provided in the center thereof, which communicates with the pressurizing chamber.

The pressurizing chamber 5 is provided adjacent to the pump chamber 2 with the bottom of the pump chamber 2 as a partition. The pressurizing chamber is provided with two ports 9 and 10, Through one of these, the pressurizing liquid is forced into the chamber. The pressurizing chamber is constructed liquid tight. The bottom 11 of the pressurizing chamber 5 is generally circular and is provided with a second rotation shaft hole 12, which communicates with a rotor chamber 4.

The rotor chamber 4 is provided adjacent to the pressurizing chamber 3 with the bottom of the pressurizing chamber as a partition. The rotor chamber is generally cylindrical and a first bearing 13 is provided at the center of the bottom and a second bearing 14 is provided in the second rotation shaft hole 12 provided in the ceiling of the chamber to cooperate with the first bearing 13.

A rotation shaft 15, which is pivotally supported by the first bearing 13, is rotatably arranged so as to extend into the pump chamber 2 through the second bearing 14; the second rotation shaft hole 12 and the first rotation shaft hole 8. An umbrella-shaped impeller base plate 16 is provided at the top of the shaft 15 which is positioned in the pump chamber. On the upper surface of the impeller base plate, a plurality of impeller blades 17 are provided generally uprightly and generally radially so that the outer edges thereof are positioned along the inner wall of the pump chamber. Through holes 18 are provided in the impeller base plate 16 between the blades 17.

A first annular seal member 20 comprising a cylindrical body portion having a through hole, by which it is mounted on the shaft 15 at the part close to the bottom of the pump chamber 2. The annular seal member 20 has an umbrella-shaped skirt portion 19, which extends obliquely downward from the lower part of the body portion so as to slightly touch the bottom of the pump chamber 2, The seal member is made of a flexible material which has no adverse effect against blood.

A second annular seal member 22 comprising a cylindrical body portion having a through hole, by which it is mounted on the shaft 15 at the part close to the bottom of the pressurizing chamber 3. The annular seal member 22 has an umbrella-shaped skirt portion 21, which extends obliquely downward from the lower part of the body portion so as to touch the bottom of the pressurizing chamber 2, The seal member is also made of a flexible material which has no adverse effect against blood.

A rotor which comprises a disc 24, on which magnets 25 are mounted, is secured to the portion of the rotation shaft 15, which is located within the rotor chamber 4. The blood pump 1 is provided with a rotating magnet means (25) at the bottom thereof in order to rotate the rotor, i.e., the impeller. The rotating magnet means is a rotating body provided with magnets corresponding to the magnets 23 of the rotor and is rotated by means of a driving means (not shown). The rotor is rotated by virtue of magnetic force of the rotating magnet means.

The above-described blood pump operates as follows.

The rotor comprising the disc 24 and the magnets 25 are rotated by rotation of the above described rotating magnet means and thus the impeller secured to the top of the shaft 15 rotates.

Blood is introduced into the blood chamber 2 through the inlet port 5 and discharged through the outlet port 6 by virtue of the centrifugal force caused by the high speed rotation of the impeller. In the pump chamber, some of the blood flows to the underside of tile base plate (hub) 16 but it returns to the upper side of the base plate 16 through the holes 18 provided in the base plate 16. Therefore, the blood, which has flowed into the underside of the impeller base plate 16, never remains in the underside of the base plate of the impeller.

Meanwhile, a pressurizing liquid is forced into the pressurizing chamber 3 through one of the inlet ports 9 and 10. When the pressurizing liquid is initially introduced through the inlet ports 9, for instance, the other port 10, in this case, is left open so that the air initially existing in the chamber is purged. When the air is removed and the pressurizing chamber 3 is filled with the pressurizing liquid, the port 10 is closed. The pressurizing liquid is continuously forced into the chamber 5 by a suitable pump means not shown.

As the pressurizing liquid is forced into the pressurizing chamber 3 with a predetermined pressure all the time, the pressurizing liquid penetrates into the blood chamber 2 through the clearance of the first rotation shaft hole 8 and the rotation shaft 15. The pressurizing liquid which has penetrated into the pump chamber 2 is replenished by the liquid forced into. Thus, the pressurizing chamber 3 is filled with the pressurizing liquid all the time.

Since the pressurizing liquid penetrates into the pump chamber 2 through the clearance between the rotation shaft hole 8 and the rotation shaft 15 with the predetermined pressure, the blood in the pump chamber does not leak into the pressurizing chamber 3. The pressurizing liquid, which penetrates into the pump chamber, lifts the skirt portion 19 of the first seal member 20 and the edge of the skirt portion lightly or scarcely contacts or entirely does not contact the bottom of the pump chamber.

In other words, the first seal member 20 secured to the rotation shaft 15 rotates but the skirt portion 19 of the seal member is slightly raised afloat from the surface of the bottom of the pump by the pressurizing liquid which penetrates through said clearance. Therefore, generation of heat by friction between the skirt portion 19 and the bottom of the pump chamber is extremely small and thus hemolysis caused by the contact of the skirt member 19 and the bottom of the pump chamber is well prevented.

When the pressure of the blood flowing into the pump chamber 2 is abruptly rises abnormally or the pressure of the pressurizing liquid in the pressurizing chamber drops abnormally for some reason, the skirt member 19 is pressed down by the pressure of the flowing blood and closes the clearance between the first rotation shaft hole 8 and the rotation shaft 15 and thus prevents the leakage of the blood into the pressurizing chamber.

In this manner, the leakage of blood from the pump chamber into the pressurizing chamber is prevented without fail by means of the first seal member and the pressurizing liquid which is forced into the pressurizing chamber even when pressure fluctuation occurs in the pump chamber or the pressurizing chamber.

In the pressurizing chamber 3, as the pressurizing liquid is forced into the skirt portion 21 of the second seal member 22 is pressed onto the surface of the bottom of the pressurizing chamber 5 and closes the clearance between the second rotation shaft hole 12 and the rotation shaft 15. This prevents the leakage of the pressurizing liquid from the pressurizing chamber 3 into the rotor chamber 4.

In the present invention, the blood pump 1 is separated into a pump chamber 2, a pressurizing chamber 3 and a rotor chamber 4. Therefore, even when blood leaks into the pressurizing chamber, it does not further leak into the rotor chamber 4. Thus troubles such as suspension of operation caused by clotting of blood in the rotor chamber are prevented.

In the above described embodiment, the driving means for the impeller is a rotor comprising a disc 24 provided with magnets 23 which is rotated by a rotating magnet means. However, the driving means is not limited thereto but any known driving means can be employed.

Driving means other than described above include a combination of a motor placed at a remote location, a flexible shaft connected to the rotation shaft of the motor and a universal joint which connects the flexible shaft and the rotation shaft.

As a pressurizing liquid, any liquid which has no adverse effect against blood can be used. However, a physiological solution containing an anti-clotting agent is preferred. The physiological solution containing anti-clotting agent is a liquid which has little or no adverse effect to the human body containing a drug which prevents clotting. An example of such physiological solution is a heparine-containing physiological saline solution. When this solution is used, clotting is effectively prevented by the solution which penetrates into the pump chamber from the pressurizing chamber.

As has been described above in detail, in accordance with this invention, the leakage of blood from the pump chamber into the pressurizing chamber is prevented by the first seal means and the pressurizing liquid which is forced into and the leakage from the pressurizing chamber to the driving device chamber is prevented by the second seal means and the pressurizing liquid. Also hemolysis which may be caused by rotation of the seal member at the vicinity of the rotation shaft in the pump chamber is prevented. That is to say, the present invention provides a small scale blood pump, which is free from the leakage and occurrence of hemolysis and clotting.

What we claim is:

1. A blood pump comprising:

a pump chamber having a inlet port and an outlet port, a pressurizing chamber having at least one port provided adjacent to the pump chamber, a rotor chamber provided adjacent to the pressurizing chamber and an impeller device comprising:

a rotation shaft rotatably supported at a center of a bottom of the rotor chamber, extending into the pump chamber through a second rotation shaft hole provided at a center of a bottom of the pressurizing chamber and a first rotation shaft hole provided at a center of a bottom of the pump chamber;

an impeller base plate secured to a top of the rotation shaft in the pump chamber, and having a plurality of impeller blades provided radially on the base plate; and a rotor secured to a lower part of the rotation shaft in the rotor chamber, wherein the rotation shaft is provided with a first annular seal member which is mounted at an upper side of the bottom of the pump chamber and has a first umbrella-shaped skirt portion made of an elastomeric material and extending from a lower part of the first annular seal member toward a surface of the upper side of the bottom of the pump chamber so as to cover a first clearance between the rotation shaft and the first rotation shaft hole, and a second annular seal member which is mounted at an upper side of the bottom of the pressurizing chamber and has a second umbrella-shaped skirt portion made of an elastomeric material and extending from a lower part of the second annular seal member toward a surface of the upper side of the bottom of the pressurizing chamber so as to cover a second clearance between the rotation shaft and the second rotation shaft hole.

2. The blood pump as claimed in claim 1, wherein the first and second annular seal members including the respective first and second umbrella-shaped skirt portions are integrally made of an elastomeric material.

3. The blood pump as claimed in claim 1, wherein the impeller base plate is umbrella-shaped.

4. The blood pump as claimed in claim 3, wherein the impeller base plate has a plurality of through holes provided between the impeller blades.

5. The blood pump as claimed in claim 1, the pressurizing chamber has two ports.

6. The blood pump as claimed in claim 1, wherein the rotor comprises a disc being secured to the lower part of the rotation shaft and magnets mounted on the disc and the rotor is magnetically rotated.

7. The blood pump as claimed in claim 1, wherein the pump chamber is shaped like an inverted funnel and the pressurizing chamber and tile rotor chamber are integrally cylindrical.

8. The blood pump as claimed in claim 1, wherein the pump chamber further comprises a blood inlet port at the top thereof and a blood outlet port at a side thereof.

* * * * *